(12) United States Patent
Ohishi

(10) Patent No.: US 7,432,924 B2
(45) Date of Patent: Oct. 7, 2008

(54) 3D DIGITAL SUBTRACTION ANGIOGRAPHY IMAGE PROCESSING APPARATUS

(75) Inventor: Satoru Ohishi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 94 days.

(21) Appl. No.: 10/649,697

(22) Filed: Aug. 28, 2003

(65) Prior Publication Data

US 2005/0046644 A1 Mar. 3, 2005

(51) Int. Cl.
*G06T 15/00* (2006.01)

(52) U.S. Cl. ............... 345/419; 345/420; 382/128; 378/62

(58) Field of Classification Search ............ 345/419, 345/420, 643; 378/62, 207; 382/132
See application file for complete search history.

(56) References Cited

U.S. PATENT DOCUMENTS

| | | | |
|---|---|---|---|
| 4,835,688 A | | 5/1989 | Kimura et al. |
| 5,712,895 A | * | 1/1998 | Negrelli et al. ............ 378/207 |
| 5,782,762 A | * | 7/1998 | Vining ..................... 600/407 |
| 5,802,133 A | | 9/1998 | Kawai et al. |
| 5,839,440 A | * | 11/1998 | Liou et al. ................. 600/431 |
| 5,852,646 A | * | 12/1998 | Klotz et al. ................... 378/8 |
| 5,956,435 A | * | 9/1999 | Buzug et al. ............... 382/283 |
| 6,370,417 B1 | * | 4/2002 | Horbaschek et al. ........ 600/424 |
| 6,493,569 B2 | * | 12/2002 | Foo et al. ................... 600/410 |
| 6,650,724 B2 | * | 11/2003 | Strobel ........................ 378/4 |
| 7,123,760 B2 | * | 10/2006 | Mullick et al. ............. 382/131 |
| 2002/0032375 A1 | | 3/2002 | Bauch et al. |
| 2005/0046644 A1 | | 3/2005 | Ohishi |

FOREIGN PATENT DOCUMENTS

JP 5-137711 6/1993

OTHER PUBLICATIONS

Foley et al., Computer Graphics Principles and Practice, 1990, Addison-Wesely Publishing Company, Inc., Second Edition, pp. 1034-1035.*
Hans-Ulrich Kauczor, et al., "Helical Computed Tomography Angiography: Technical Considerations and Clinical Applications", Radiography, vol. 3, No. 1, XP-004797823, Feb. 1997, pp. 3-15.
U.S. Appl. No. 11/282,657, filed Nov. 21, 2005, Ohishi.

* cited by examiner

*Primary Examiner*—Ulka Chauhan
*Assistant Examiner*—Said Broome
(74) *Attorney, Agent, or Firm*—Oblon, Spivak, McClelland, Maier & Neustadt, P.C.

(57) ABSTRACT

A 3D image processing apparatus comprises a storing unit storing mask images corresponding to projection directions associated with a subject contrast images corresponding to the projection directions, a subtracting unit generating subtraction images by subtracting the mask images from the contrast images, a reconstruction unit reconstructing first volume data from the mask images and reconstructs second volume data from the subtraction images, an image processing unit generating a first 3D image representing a bone structure and/or a soft tissue structure from the first volume data, and generates a second 3D image representing a contrasted blood vessel from the second volume data, an image synthesizing unit generating a synthetic image by synthesizing the first 3D image with the second 3D image, and a displaying unit displaying the synthetic image.

8 Claims, 10 Drawing Sheets

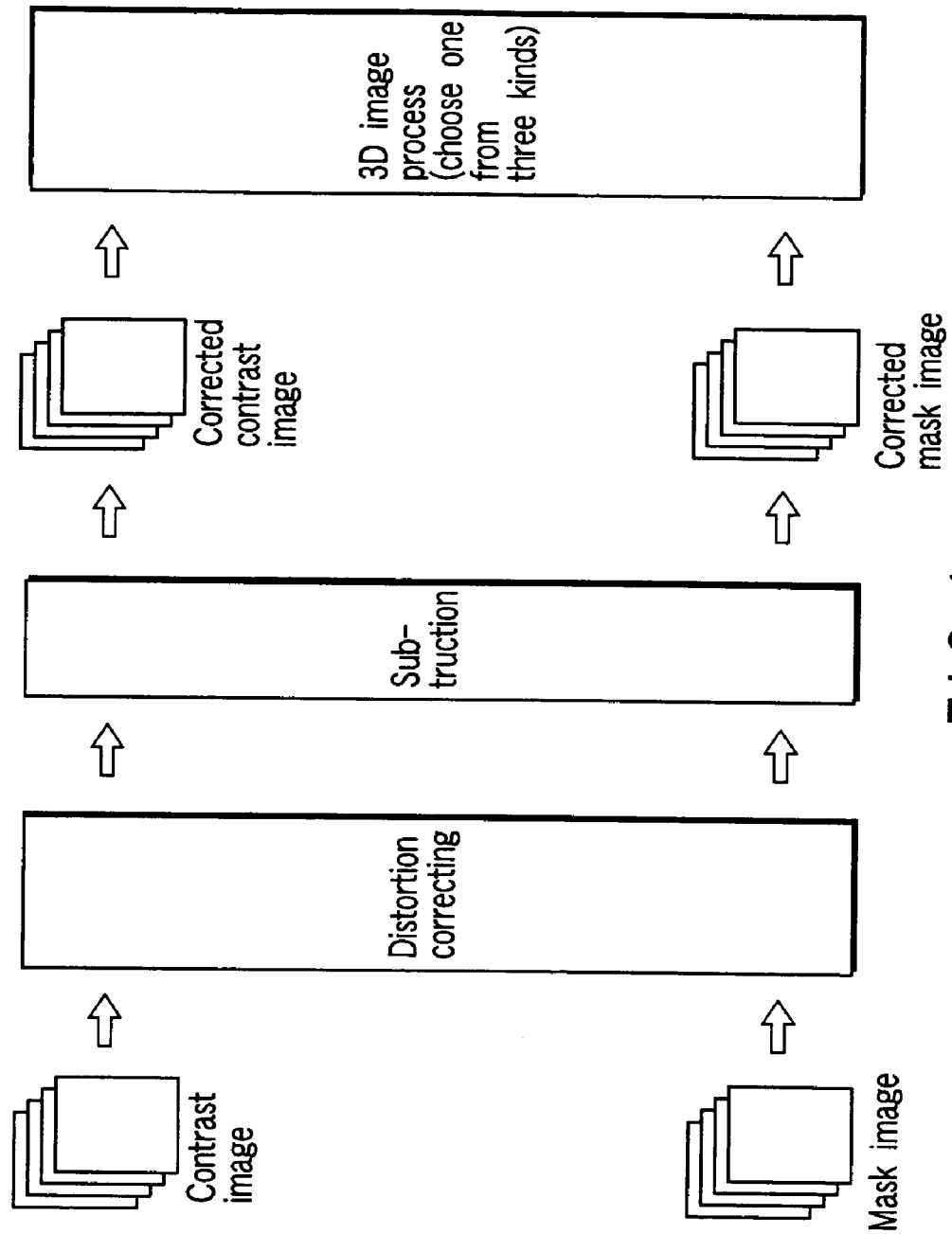
F I G. 4

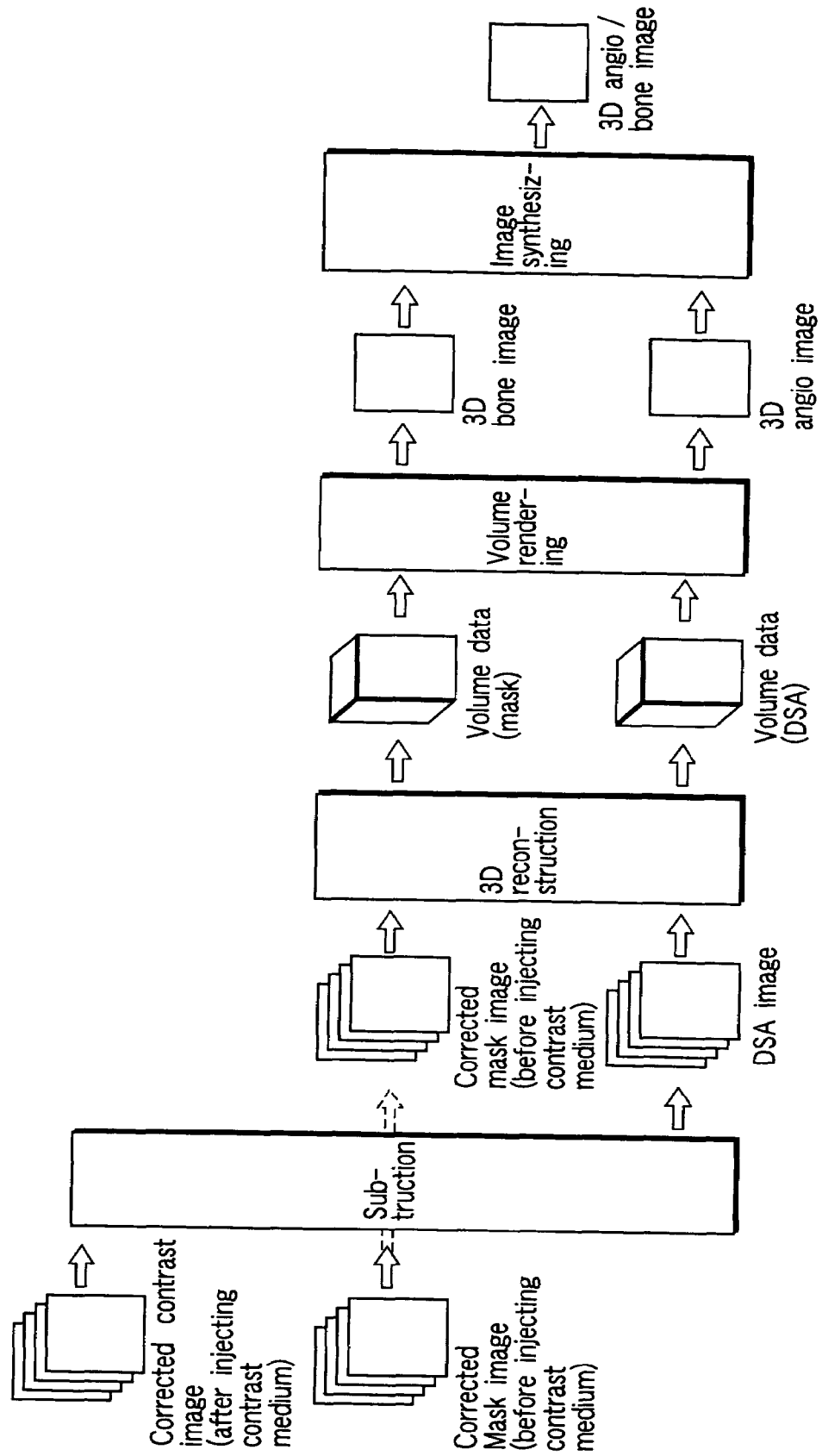
F I G. 5

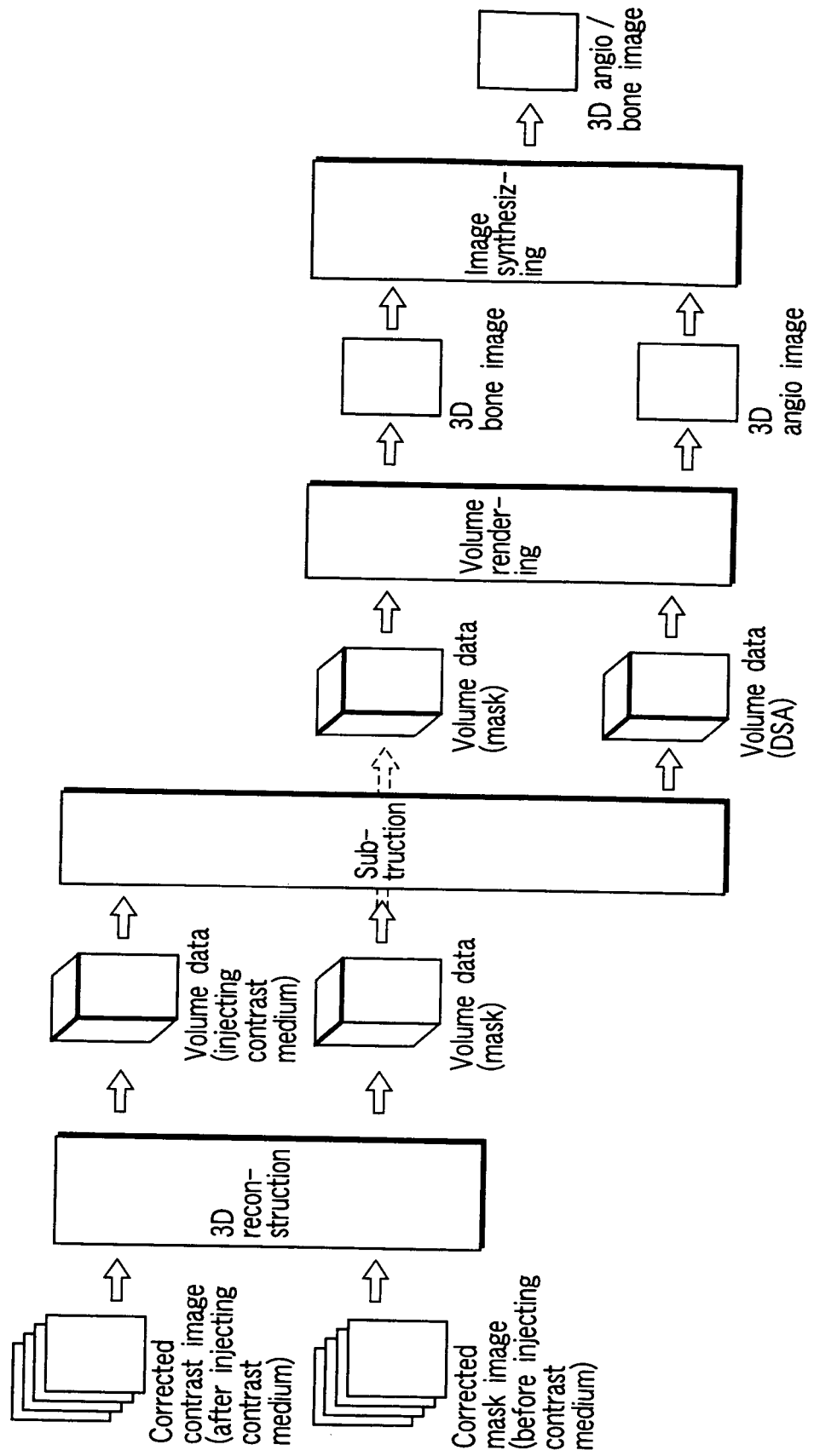
F I G. 6

3D DIGITAL SUBTRACTION ANGIOGRAPHY IMAGE PROCESSING APPARATUS

BACKGROUND OF THE INVENTION

1. Field of the Invention

The present invention relates to a 3D image processing apparatus.

2. Description of the Related Art

A highly precise blood vessel structure can be extracted from a 3D-DSA image reconstructed from a plurality of DSA (Digital Subtraction Angiography) images corresponding to a plurality of projection directions. 3D-DSA images therefore are very useful for IVR support. In subtraction processing, however, the data of bones and soft tissues, other than contrasted blood vessels, are removed. 3D-DSA images therefore include no bone structure. For this reason, the 3D-DSA images are low in utility for surgical operation support. A 3D-DA image reconstructed from a plurality of DA (Digital Angiography) images corresponding to a plurality of projection directions includes a bone structure and blood vessel structure. An observer can therefore grasp the position of the blood vessel relative to the bone from the 3D-DA image. However, it is difficult to separate blood vessels from bones and soft tissues in a 3D-DSA image clearly.

BRIEF SUMMARY OF THE INVENTION

It is an object of the present invention to separate blood vessels from bones clearly, and to display blood vessels in high definition.

According to a aspect of the present invention, there is provided the 3D image processing apparatus comprises a storing unit storing mask images corresponding to projection directions associated with a subject contrast images corresponding to the projection directions, a subtracting unit generating subtraction images by subtracting the mask images from the contrast images, a reconstruction unit reconstructing first volume data from the mask images and reconstructs second volume data from the subtraction images, an image processing unit generating a first 3D image representing a bone structure and/or a soft tissue structure from the first volume data, and generates a second 3D image representing a contrasted blood vessel from the second volume data, an image synthesizing unit generating a synthetic image by synthesizing the first 3D image with the second 3D image, and a displaying unit displaying the synthetic and/or individual images.

BRIEF DESCRIPTION OF THE SEVERAL VIEWS OF THE DRAWING

FIG. 4 is a view showing the pre-processing in the 3D image processing apparatus in FIG. 1;

FIG. 5 is a view showing the first processing sequence in the 3D image processing apparatus in FIG. 1;

FIG. 6 is a view showing the second processing sequence in the 3D image processing apparatus in FIG. 1;

DETAILED DESCRIPTION OF THE INVENTION

Figure 1:
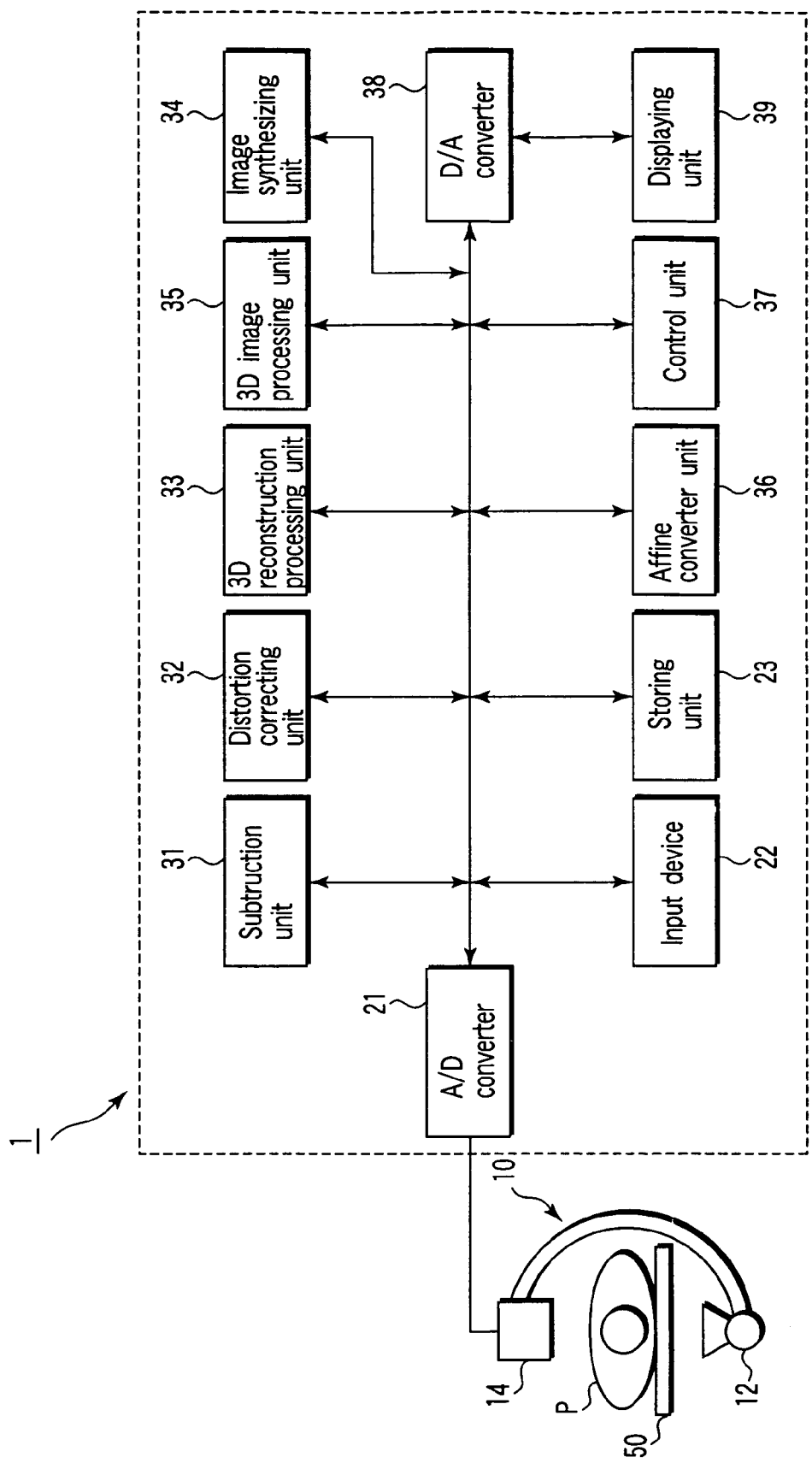
FIG. 1 is a block diagram showing the arrangement of a 3D image processing apparatus according to an embodiment.
Figure 2:
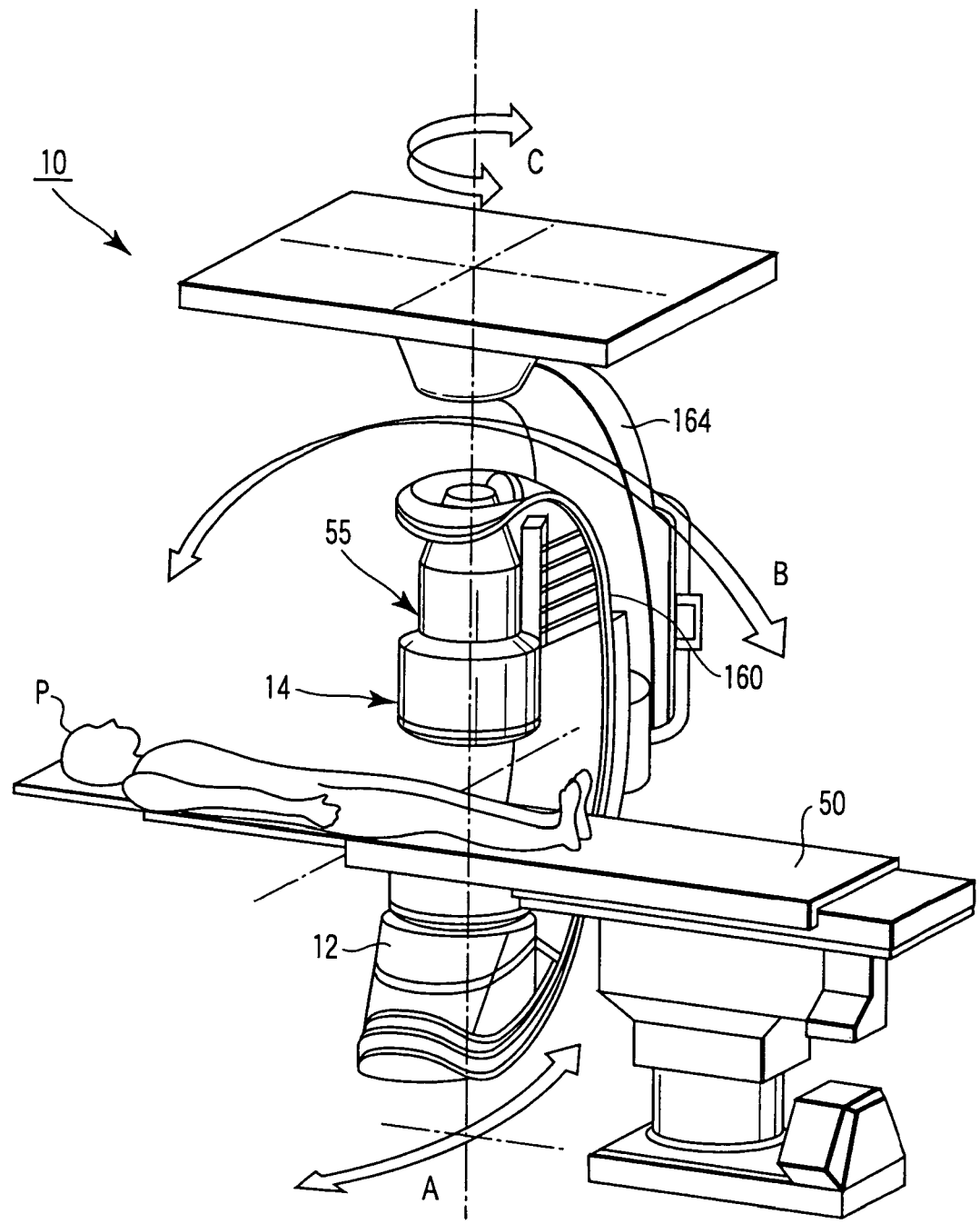
FIG. 2 is a perspective view showing the outer appearance of an X-ray imaging mechanism in FIG. 1.

As shown in FIG. 1, a 3D X-ray diagnosing apparatus has an X-ray imaging mechanism 10 and 3D image processing apparatus 1. As shown in FIG. 2, the X-ray imaging mechanism 10 has an X-ray tube 12 and detection system 14. The detection system 14 is constituted by an image intensifier and TV camera. The detection system 14 may be formed from a flat panel detector. The X-ray tube 12 is mounted on a C-arm 160 together with the detection system 14. An object P to be examined is placed on a top 50 of a bed is placed between the X-ray tube 12 and the detection system 14. The C-arm 160 is supported by a support 164 suspended from the ceiling. The C-arm 160 can rotate along three orthogonal axes A, B, and C.

The 3D image processing apparatus 1 includes a control unit 37 serving as a main component, an A/D converter 21, an input device 22, a storing unit 23, a subtracting unit 31, a distortion correcting unit 32, an affine converter 36, a 3D reconstruction processing unit 33, a 3D image processing unit 35, an image synthesizing unit 34, a D/A converter 38, and a displaying unit 39. The A/D converter 21 is connected to the detection system 14. The D/A converter 38 is connected to the displaying unit 39. The input device 22 has a keyboard and mouse. The storing unit 23 stores various data such as image data, volume data, and synthetic image data input through the A/D converter 21. The subtracting unit 31 has a function of subtracting image data and a function of subtracting image data or volume data. In the subtracting process of the former, a logarithm natural of two data is computed, and the two data are subtracted after that. In the subtracting process of the latter, a two data are subtracted directly. The former is named as the first subtracting process, and the latter is named as the second subtracting process in the following. The distortion correcting unit 32 has distortion correction processing for correcting image distortion to originate in the Image Intensifie. The affine converter 36 performs enlargement processing and movement processing.

The 3D reconstruction processing unit 33 reconstructs volume data from a plurality of image data corresponding to a plurality of projection directions. The 3D image processing unit 35 generates 3D image data from volume data by surface rendering processing. The image synthesizing unit 34 generates synthetic image data by synthesizing two or more kinds of 3D images.

The operation of this embodiment will be described next. A contrast media is injected into a blood vessel of the object. Before the contrast media is injected into the object, a plurality of image data corresponding to a plurality of projection directions are acquired. Images acquired before injection of the contrast media are called mask images. The mask images include an image of a bone and an image of a soft tissue. Pixel values in the respective images reflect transmittances unique to the bone and soft tissue.

After the contrast media is injected, a plurality of image data corresponding to a plurality of projection directions are acquired. Images acquired after injection of the contrast media are called contrast images. The plurality of projection directions to which the plurality of contrast images correspond coincide with the plurality of projection directions to which the plurality of mask images correspond. The contrast images include an image of the bone, an image of the soft tissue, and an image of the blood vessel. A pixel value in the image of the bone retlects a transmittance unique to the bone. A pixel value in the image of the soft tissue reflects a transmittance unique to the soft tissue. A pixel value in the image of the blood vessel reflects a transmittance unique to the contrast media in the blood vessel instead of the blood vessel. The transmittance of the contrast media is much lower than that of the blood vessel.

In practice, for example, imaging is repeated 200 times at 1°-intervals while the C-arm 160 rotates (A or B) at high speed. As a consequence, 200 mask images (200 frames) are obtained. The 200 mask images correspond to 200 projection directions. The 200 contrast images obtained by imaging after injection of the contrast media correspond to the 200 projection directions. The 200 contrast images respectively correspond to the 200 mask images. A given mask image coincides in projection direction with a corresponding contrast image.

Figure 3A:
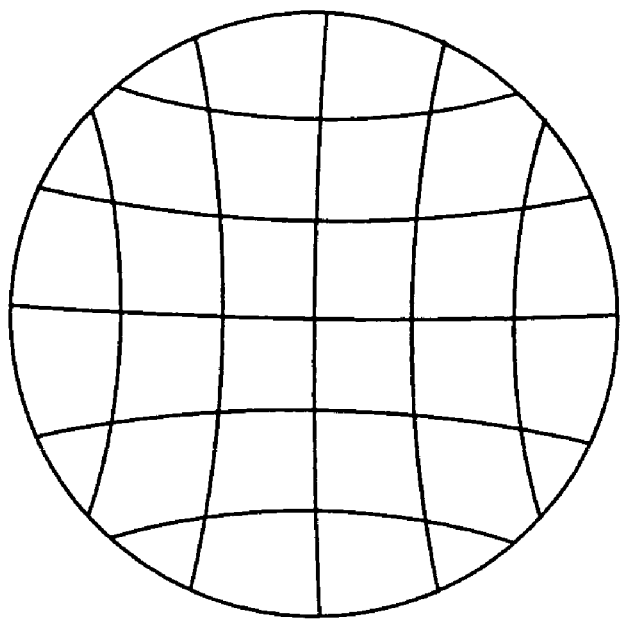
FIGS. 3A and 3B are supplementary views of distortion correction processing in a 3D reconstruction processing unit in FIG. 1.
Figure 3B:
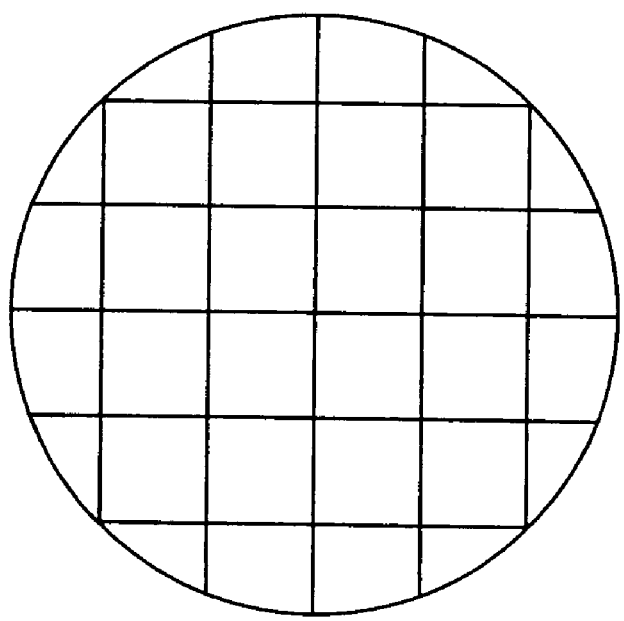

The data of the 200 mask images are stored in the storing unit 23. Likewise, the data of the 200 contrast images are stored in the storing unit 23. These mask image data and contrast image data are subjected to distortion correction processing by the distortion correcting unit 32, as shown in FIG. 4. For the sake of simplicity, consider, as distortion correction processing, processing using a phantom having wires arranged at equal intervals vertically and horizontally in the form of a square lattice. When imaging is performed after this phantom is placed on the detection surface of the detection system 14, a projection image of the phantom ideally has a square lattice shape, as shown in FIG. 3B. In practice, however, the projection image of the phantom undergoes pincushion distortion due to the shape of the detection surface of the detection system 14 and sigmoid distortion due to geomagnetism, as shown in FIG. 3A. For this reason, the distorted image data shown in FIG. 3A is acquired in advance, and the intersections of the wires are extracted as lattice points from this distorted image data. These lattice points should be arranged at equal intervals in the absence of distortion. Therefore, correction vectors for arraying the lattice points at equal intervals are obtained for each lattice point. The mask and contrast images are corrected in accordance with the correction vectors. Points other than the lattice points are corrected by using the data of neighboring lattice points. Note that since different distortion distributions appear at different angles, a distortion distribution table measured from acquired angle-specific phantom projection images is held, and distortion is corrected on the basis of the table.

The subtracting unit 31 corrects density non-uniformlty in a mask image. Likewise, the subtracting unit 31 corrects density non-uniformlty in a contrast image. The processing for correcting density non-uniformity subtracts a image for correcting density non-uniformlty from a mask or contrast image in the first subtracting process. The image for correcting density non-uniformlty is obtained by imaging in a state wherein nothing other than air is interposed between the X-ray tube 12 and the detection system 14.

This embodiment provides three kinds of 3D image processes for separately generating 3D image data representing a bone structure and 3D image data representing a contrasted blood vessel structure. The three kinds of 3D image processes are shown in FIGS. 4, 5, and 6. A desired one of the three kinds of 3D image processing is selected by an operator through the input device 22. An angio-image and bone image are generated by the selected process. A synthetic image of the generated angio-image and bone image is displayed.

The three kinds of 3D image processes will be sequentially described below.

Figure 8A:
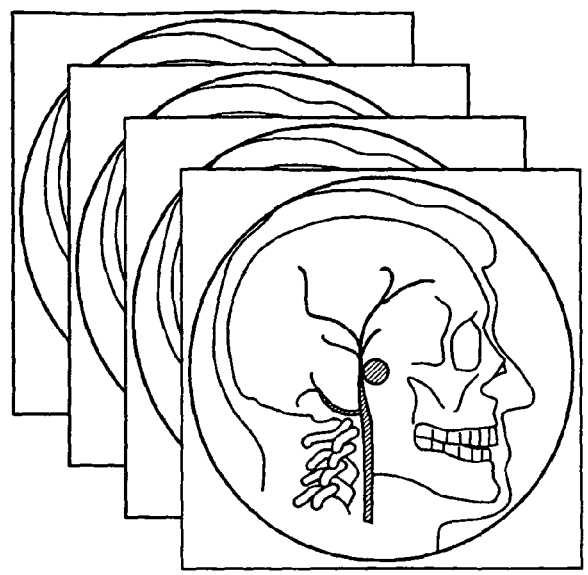
FIG. 8A is a view showing contrast images.
Figure 8B:
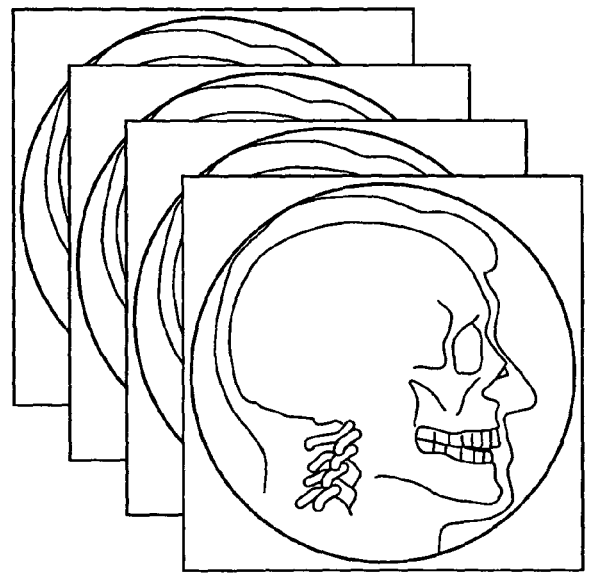
FIG. 8B is a view showing mask images.
Figure 8C:
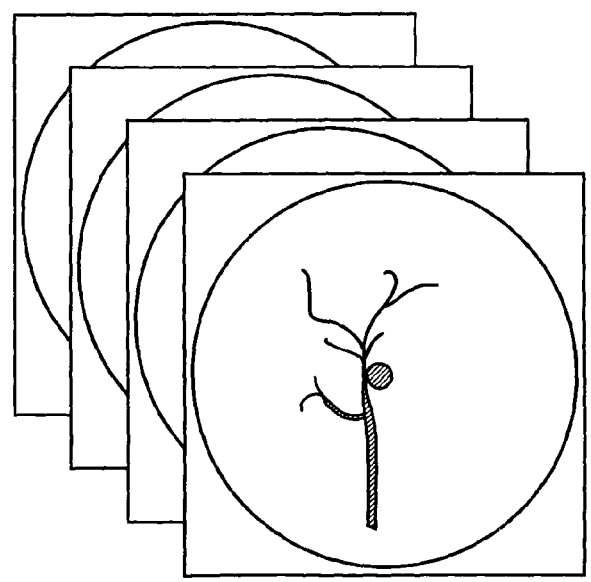
FIG. 8C is a view showing DSA images.

As shown in FIG. 5, in the first 3D image process, first of all, the subtracting unit 31 subtracts a plurality of corrected mask images (see FIG. 8B) in different projection directions from a plurality of corrected contrast images (see FIG. 8A) in different projection directions in the second subtracting process. When it says concretely, the respective corrected mask images are subtracted from the corresponding corrected contrast images in the same projection directions as those of the mask images. As a consequence, a plurality of DSA images (see FIG. 8C) are generated. Each corrected mask image includes an image of a bone and an image of a soft tissue. Each corrected contrast image includes an image of the bone, an image of the soft tissue, and an image of the contrasted blood vessel. Each DSA image substantially includes only an image of the contrasted blood vessel.

Figure 9A:
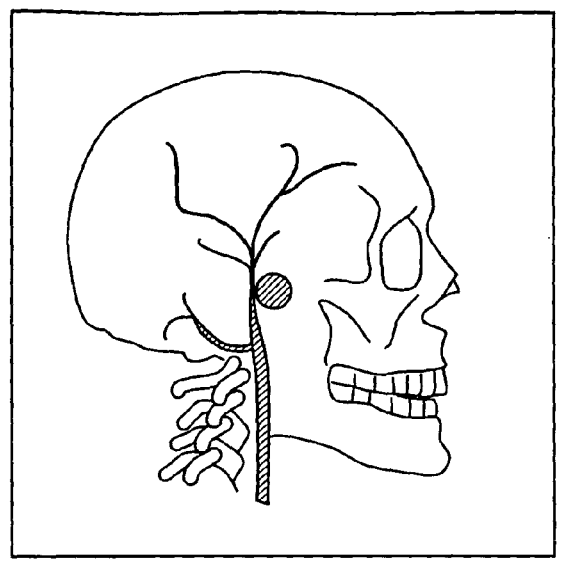
FIG. 9A is a view showing volume data corresponding to the contrast images.
Figure 9B:
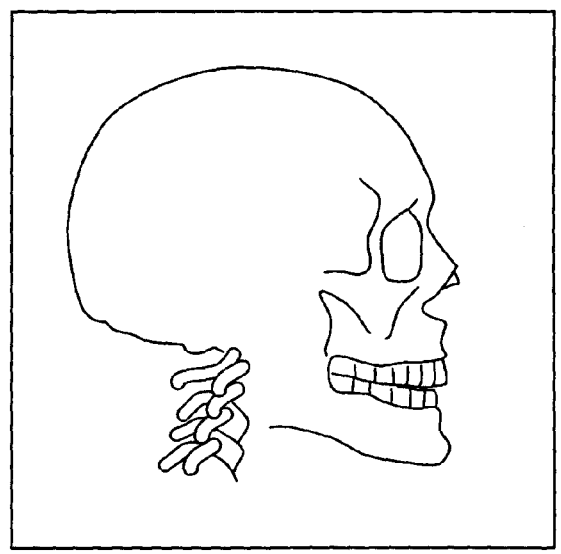
FIG. 9B is a view showing volume data corresponding to the mask images.
Figure 9C:
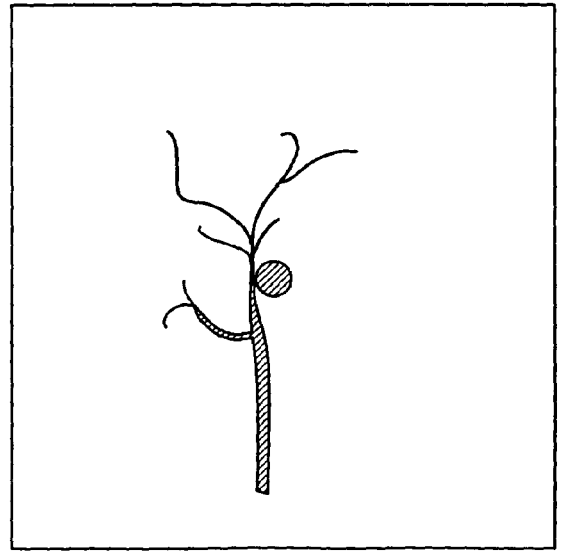
FIG. 9C is a view showing volume data corresponding to the DSA images.

A plurality of mask images are subjected to 3D reconstruction processing by the 3D reconstruction processing unit 33. As a consequence, volume data (mask) is generated (see FIG. 9B). The volume data (mask) includes the 3D structure of the bone, the 3D structure of the soft tissue. A plurality of DSA images are subjected to 3D reconstruction processing by the 3D reconstruction processing unit 33. As a consequence, volume data (DSA) is generated (see FIG. 9C). The volume data (DSA) includes only the 3D structure of the contrasted blood vessel.

As a reconstruction method, the filtered back projection method proposed by Feldkamp et al. is generally used. An appropriate convolution filter such as a Shepp-Logan filter or Ramachandran filter is applied to the 200 DSA images. The 200 DSA images processed by the convolution filter are then subjected to back projection operation. As a consequence, volume data (DSA) is generated. Likewise, an appropriate convolution filter is applied to the 200 corrected mask images. The 200 corrected mask images processed by the convolution filter are then subjected to back projection operation. As a consequence, volume data (mask) is generated.

In this case, a reconstruction region is defined as a cylinder inscribed in an X-ray beam from the X-ray tube 12 in all directions. The inside of this cylinder is three-dimensionally discretized with a length d at the central portion of the reconstruction region projected by the width of one detection element of the detection system 14, and a reconstructed image based on the data of each discrete point must be obtained. Although an example of the discrete interval is described, this value may differ depending on the apparatus or maker. Basically, therefore, it suffices if the discrete interval defined for each apparatus be used.

The volume data (mask) is subjected to surface rendering processing by the 3D image processing unit 35. This generates a 3D image (3D bone image) representing the 3D structure of the bone. The volume data (DSA) is subjected to surface rendering processing by the 3D image processing unit 35. This generates a 3D image (3D angio-image) representing the 3D structure of the contrasted blood vessel.

The surface rendering processing is processing of rearranging volume data into a 2D pixel matrix so as to render the data on the displaying unit 39 having a 2D display screen. The image data is arranged as 2D matrix data but expresses the 3D structure of the object. In this case, therefore, this image will be referred to as a 3D image in particular. In surface rendering processing, first of all, the coordinate position of the volume data is converted to a viewpoint coordinate system. The viewpoint coordinate system for the volume data (mask) coincides with that for the volume data (DSA). In the surface rendering processing, occlusion processing and shading processing of shading an object surface are executed with respect to the converted volume data. As a consequence, 3D image data is generated. Surface rendering processing for the volume data (mask) is performed for only voxels having voxel values (CT values) within a range corresponding to the bone. This generates a 3D bone image. Surface rendering processing for the volume data (DSA) is performed for only voxels having voxel values (CT values) within a range corresponding to the contrasted blood vessel. This generates a 3D angio-image.

The image synthesizing unit 34 generates the 3D image (mask) based on the volume data (mask) and generates the 3D image (DSA) originated from the volume data (DSA), by using the hidden plane removal processing. The image synthesizing unit 34 synthesizs the 3D image (mask) and the 3D image (DSA). As a consequence, a synthetic image (3D angio/bone image) is generated.

The 3D image processing of this embodiment is characterized in that the 3D image (3D bone image) representing the 3D structure of the bone and the 3D image (3D angio-image) representing the 3D structure of the contrasted blood vessel are independently generated. Therefore, the 3D structure of the blood vessel can be displayed by the color which is different from the 3D structure of the bone. The 3D structure of the blood vessel can be identified from the 3D structure of the bone. The observer can recognize the position of the blood vessel to the bone.

Figure 10:
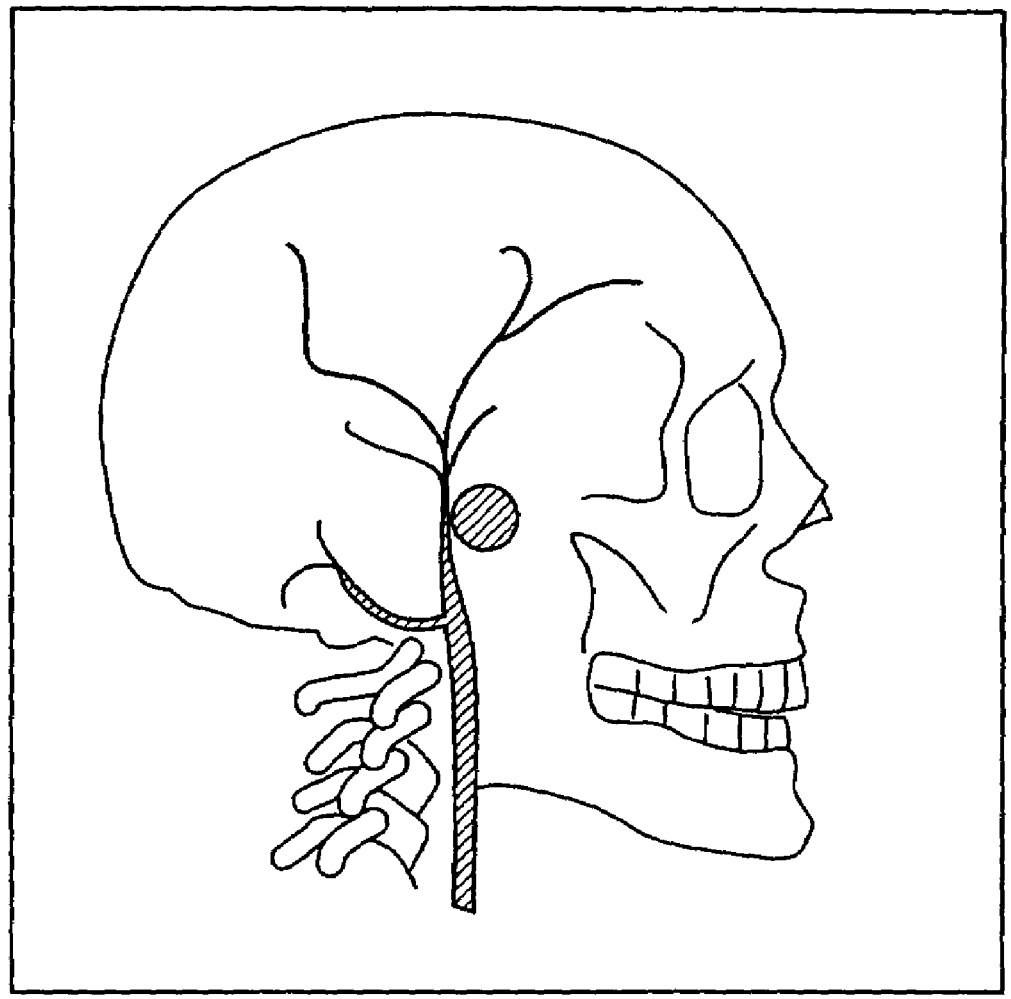
FIG. 10 is a view showing a 3D angio/bone image.

The 3D angio/bone image is displayed on the displaying unit 39 (see FIG. 10). In accordance with specifying operation by the operator, 3D angio display image or 3D bone display image is singly displayed on the displaying unit 39 in place of the 3D angio/bone image. The 3D displaying method is not limited to the surface rendering method. The volume rendering method, MIP(Maximum Intensity Projection), MinIP(Minimum Intensity Projection) or VED(Virtual Endoscopic Display) may be used.

As shown in FIG. 6, in the second 3D image process, 3D reconstruction processing is performed before subtraction processing. A plurality of mask images are subjected to 3D reconstruction processing by the 3D reconstruction processing unit 33. This generates volume data (mask). The volume data (mask) includes the 3D structure of the bone, the 3D structure of the soft tissue.

A plurality of contrast images are subjected to 3D reconstruction processing by the 3D reconstruction processing unit 33. This generates volume data (after injection of the contrast media) (see FIG. 9A). The volume data (after injection of the contrast media) includes the 3D structure of the bone, the 3D structure of the soft tissue, and the 3D structure of the contrasted blood vessel.

The volume data (mask) is subtracted from the volume data (contrast) by the second subtraction processing. As a consequence, volume data (DSA) including only the 3D structure of the contrasted blood vessel is generated.

The generated volume data (mask) and volume data (DSA) are subjected to the same processing as that in the first 3D image process.

Figure 7:
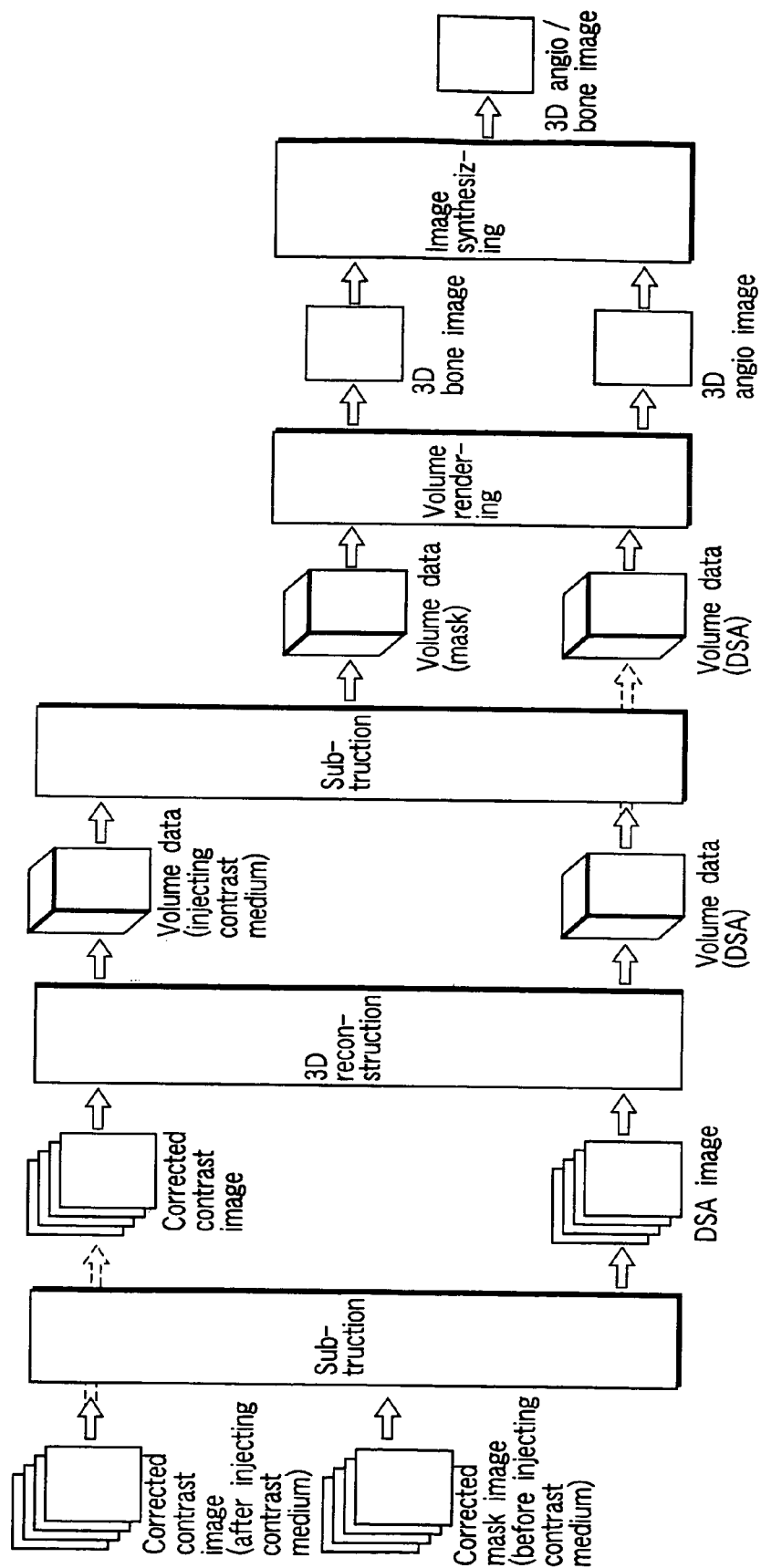
FIG. 7 is a view showing the third processing sequence in the 3D image processing apparatus in FIG. 1.

As shown in FIG. 7, in the third 3D image process, as in the first 3D image process, first of all, a plurality of mask images are subtracted from a plurality of contrast images to generate a plurality of DSA images by the second subtraction processing.

The 3D reconstruction processing unit 33 then generates volume data (after injection of the contrast media) from a plurality of contrast images, and generates volume data (DSA) from a plurality of DSA images.

The volume data (DSA) is subtracted from the volume data (after injection of the contrast media). This generates volume data (mask) including the 3D structure of the bone, the 3D structure of the soft tissue.

The generated volume data (mask) and volume data (DSA) are subjected to the same processing as that in the first 3D image process.

In this embodiment, volume data including a bone structure and volume data including a contrasted blood vessel structure are separately generated from contrast images and mask images. Surface rendering is separately applied to the volume data including the bone structure and the volume data including the contrasted blood vessel structure. A 3D image representing the bone structure and a 3D image representing the blood vessel structure are generated. These two images are synthesized. The resultant image is then displayed. This makes it possible to display the precise blood vessel structure together with the bone structure.

In this case, the X-ray imaging apparatus incorporates the 3D reconstruction processing unit and 3D image processing unit. However, the present invention is not limited to this, and the X-ray imaging apparatus, 3D reconstruction processing unit, and 3D image processing unit may be independently arranged in an allowable combination. Soft tissues such as internal organs may be extracted in place of the bone from the volume data (mask).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An image processing apparatus comprising:

an input configured to receive digital images of an object viewed from a plurality of projection directions both with and without a contrast medium injected into the object, respectively contrast images and mask images;

a storage unit configured to store the digital images;

a subtraction unit configured to subtract the digital images from each other to generate digital subtraction images;

a reconstruction unit configured to generate 3D digital images from plural digital images viewed from the plurality of projection directions;

an image processing unit configured to carry out surface rendering processing of the 3D digital images to generate surface rendered digital images for display;

an image synthesizing unit configured to generate a synthesis of two of the surface rendered digital images;

a display unit configured to display the synthesized digital images; and an input device configured to be used by an operator to select one of three modes of 3D image processing on the object, the apparatus configured to operate according to this selection, such that in the first mode:

mask and contrast images are input and subtracted by the subtraction unit to generate digital subtraction images which are separately processed by the reconstruction unit to generate 3D digital mask and subtraction images, which are then separately processed by the image processing unit to generate surface rendered digital mask and subtraction images, which are then synthesized by the image synthesizing unit into a combined 3D digital image which is displayed on the display unit;

in the second mode:

mask and contrast images are input and separately processed by the reconstruction unit to generate 3D digital mask and contrast images which are then subtracted by the subtraction unit to generate 3D digital subtraction images, the 3D digital mask and subtraction images then being separately processed by the image processing unit to generate surface rendered digital mask and subtraction images, which are then synthesized by the image synthesizing unit into a combined 3D digital image which is displayed on the display unit;

and in the third mode:

mask and contrast images are subtracted in the subtraction unit to generate digital subtraction images viewed from the plurality of projection directions, then the digital subtraction images and the digital contrast images are separately processed by the reconstruction unit to generate 3D digital contrast and subtraction images, which are then subtracted from each other in the subtraction unit to generate 3D digital mask images, the 3D digital mask and subtraction images then being separately processed by the reconstruction unit to generate 3D digital mask and subtraction images, which are then separately processed by the image processing unit to generate surface rendered digital mask and subtraction images, which are then synthesized by the image synthesizing unit into a combined 3D digital image which is displayed on the display unit.

2. An image processing apparatus comprising:

an input configured to receive digital images of an object viewed from a plurality of projection directions both with and without a contrast medium injected into the object, respectively contrast images and mask images;

a storage unit configured to store the digital images;

a subtraction unit configured to subtract the digital images from each other to generate digital subtraction images;

a reconstruction unit configured to generate 3D digital images from plural digital images viewed from the plurality of projection directions;

an image processing unit configured to carry out surface rendering processing of the 3D digital images to generate surface rendered digital images for display;

an image synthesizing unit configured to generate a synthesis of two of the surface rendered digital images;

a display unit configured to display the synthesized digital images;

the apparatus being arranged such that mask and contrast images are input and separately processed by the reconstruction unit to generate 3D digital mask and contrast images which are then subtracted by the subtraction unit to generate 3D digital subtraction images, the 3D digital mask and subtraction images then being separately processed by the image processing unit to generate surface rendered digital mask and subtraction images, which are then synthesized by the image synthesizing unit into a combined 3D digital image which is displayed on the display unit.

3. An image processing apparatus comprising:

an input configured to receive digital images of an object viewed from a plurality of projection directions both with and without a contrast medium injected into the object, respectively contrast images and mask images;

a storage unit configured to store the digital images;

a subtraction unit configured to subtract the digital images from each other to generate digital subtraction images;

a reconstruction unit configured to generate 3D digital images from plural digital images viewed from the plurality of projection directions;

an image processing unit configured to carry out surface rendering processing of the 3D digital images to generate surface rendered digital images for display;

an image synthesizing unit configured to generate a synthesis of two of the surface rendered digital images;

a display unit configured to display the synthesized digital images;

the apparatus being arranged such that mask and contrast images are subtracted in the subtraction unit to generate digital subtraction images viewed from the plurality of projection directions, then the digital subtraction images and the digital contrast images are separately processed by the reconstruction unit to generate 3D digital contrast and subtraction images, which are then subtracted from each other in the subtraction unit to generate 3D digital mask images, the 3D digital mask and subtraction images then being separately processed by the reconstruction unit to generate 3D digital mask and subtraction images, which are then separately processed by the image processing unit to generate surface rendered digital mask and subtraction images, which are then synthesized by the image synthesizing unit into a combined 3D digital image which is displayed on the display unit.

4. An image processing apparatus comprising:

an input configured to receive digital images of an object viewed from a plurality of projection directions both with and without a contrast medium injected into the object, respectively "contrast" images and "mask" images;

a storage unit configured to store the digital images;

a subtraction unit configured to subtract the digital images from each other to generate digital subtraction images;

a reconstruction unit configured to generate 3D digital images from plural digital images viewed from the plurality of projection directions;

an image processing unit configured to carry out surface rendering processing of the 3D digital images to generate surface rendered digital images for display;

an image synthesizing unit configured to generate a synthesis of two of the surface rendered digital images;

a display unit configured to display the synthesised digital images; and a distortion correction unit with a stored distortion distribution table containing correction vectors for use by the distortion correction unit to correct the mask and contrast images for pincushion distortion and sigmoid distortion;

the apparatus being configured to acquire the mask and contrast images and to correct them in the distortion correction unit;

and then either:

mask and contrast images are subtracted in the subtraction unit to generate digital subtraction images viewed from the plurality of projection directions, then the digital subtraction images and the digital contrast images are separately processed by the reconstruction unit to generate 3D digital contrast and subtraction images, which are then subtracted from each other in the subtraction unit to generate 3D digital mask images, the 3D digital mask and subtraction images then being separately processed by the reconstruction unit to generate 3D digital mask and subtraction images, which are then separately processed by the image processing unit to generate surface rendered digital mask and subtraction images, which are then synthesized by the image synthesizing unit into a combined 3D digital image which is displayed on the display unit;

or mask and contrast images are input and separately processed by the reconstruction unit to generate 3D digital mask and contrast images which are then subtracted by the subtraction unit to generate 3D digital subtraction images, the 3D digital mask and subtraction images then being separately processed by the image processing unit to generate surface rendered digital mask and subtraction images, which are then synthesized by the image synthesizing unit into a combined 3D digital image which is displayed on the display unit;

or mask and contrast images are subtracted in the subtraction unit to generate digital subtraction images viewed from the plurality of projection directions, then the digital subtraction images and the digital contrast images are separately processed by the reconstruction unit to generate 3D digital contrast and subtraction images, which are then subtracted from each other in the subtraction unit to generate 3D digital mask images, the 3D digital mask and subtraction images then being separately processed by the reconstruction unit to generate 3D digital mask and subtraction images, which are then separately processed by the image processing unit to generate surface rendered digital mask and subtraction images, which are then synthesized by the image synthesizing unit into a combined 3D digital image which is displayed on the display unit.

5. An apparatus according to any one of claims 1 to 4, wherein the image synthesizing unit is configured to display the synthesized images in different respective colors.

6. An apparatus according to any one of claims 1 to 4, wherein the image synthesizing unit is configured to assign color information to the mask and subtraction images independently.

7. An apparatus according to any one of claims 1 to 4, wherein the image processing unit is configured to carry out surface rendering by volume rendering processing.

8. An apparatus according to any one of claims 1 to 4, configured such that the display unit singly displays the 3D mask image or the 3D subtraction image in place of the synthesized image in accordance with a user instruction.

* * * * *